(12) United States Patent
Mikumo et al.

(10) Patent No.: US 8,222,327 B2
(45) Date of Patent: Jul. 17, 2012

(54) PLASMA STERILIZATION INDICATOR

(75) Inventors: Masao Mikumo, Tokyo (JP); Kenji Kazama, Tokyo (JP)

(73) Assignee: Hogy Medical Co., Ltd., Tokyo (JP)

( * ) Notice: Subject to any disclaimer, the term of this patent is extended or adjusted under 35 U.S.C. 154(b) by 0 days.

(21) Appl. No.: 12/920,594

(22) PCT Filed: Sep. 30, 2008

(86) PCT No.: PCT/JP2008/067713
§ 371 (c)(1),
(2), (4) Date: Sep. 3, 2010

(87) PCT Pub. No.: WO2009/113197
PCT Pub. Date: Sep. 17, 2009

(65) Prior Publication Data
US 2011/0009535 A1  Jan. 13, 2011

(30) Foreign Application Priority Data
Mar. 10, 2008  (JP) ................ P2008-059165

(51) Int. Cl.
*C08K 5/23* (2006.01)
(52) U.S. Cl. ............... 524/99; 524/190; 524/196
(58) Field of Classification Search ............... 524/190, 524/99, 196
See application file for complete search history.

(56) References Cited

U.S. PATENT DOCUMENTS

| 6,267,242 | B1 | 7/2001 | Nagata et al. | |
|---|---|---|---|---|
| 2002/0121629 | A1 | 9/2002 | Mikumo et al. | |
| 2003/0194346 | A1 | 10/2003 | Read | |
| 2007/0134797 | A1 | 6/2007 | Read | |
| 2008/0267811 | A1* | 10/2008 | Yamaguchi et al. | 422/3 |

FOREIGN PATENT DOCUMENTS

| JP | 51-49805 | 4/1976 |
|---|---|---|
| JP | 55-069671 | 5/1980 |
| JP | 56-95053 | 8/1981 |
| JP | 59-036172 | 2/1984 |
| JP | 59-124956 | 7/1984 |
| JP | 59-219375 | 12/1984 |
| JP | 62-121777 | 6/1987 |
| JP | 05-001252 | 1/1993 |
| JP | 11-178904 | 7/1999 |
| JP | 2001-174449 | 6/2001 |
| JP | 2002-011081 | 1/2002 |
| JP | 2002-071570 | 3/2002 |
| JP | 2002-294113 | 10/2002 |
| JP | 2002-303618 | 10/2002 |
| JP | 2002-541466 | 12/2002 |
| JP | 2003-102811 | 4/2003 |
| JP | 3418937 | 4/2003 |
| JP | 3435505 | 6/2003 |
| JP | 2004-101488 | 4/2004 |
| JP | 2004-203984 | 7/2004 |
| JP | 2004-298479 | 10/2004 |
| JP | 2005-514112 | 5/2005 |
| JP | 2005-315828 | 11/2005 |
| JP | 2007-040785 | 2/2007 |
| WO | 98/46279 | 10/1998 |
| WO | 2005/095948 | 10/2005 |

OTHER PUBLICATIONS

Machine translation of JP 11-178904. Jul. 1999.*
International Search Report—PCT/JP2008/067713—Jan. 27, 2009.

* cited by examiner

*Primary Examiner* — Ling Choi
*Assistant Examiner* — John Uselding
(74) *Attorney, Agent, or Firm* — Young & Thompson

(57) ABSTRACT

A novel indicator for plasma sterilization utilizes an azo dye which has been known and used for preparing indicator for ethylene oxide gas sterilization and indicator for heat sterilization, and which exhibits a quick change of color upon the cold plasma sterilization process using an oxidizing gas such as hydrogen peroxide, the change of color being indicated as a clear change of the color tone. The azo dye is used in combination with a compound containing a mercapto group or a dithiocarbamyl group therein as the compound capable of reacting with the azo dye upon the plasma sterilization treatment, and thereby bringing discoloration into the azo dye. Moreover, in combination with them, a polyhydric phenol compound or an aromatic carboxylic acid may be further used as antifading agent for discolored azo dye which is produced during the plasma sterilization process in order to stabilize the occurrence of discoloration.

6 Claims, No Drawings

PLASMA STERILIZATION INDICATOR

TECHNICAL FIELD

This invention is related to an indicator for plasma sterilization, which is used when a medical tool undergoes sterilization according to the cold plasma sterilization process with an oxidizing gas such as hydrogen peroxide gas, in order to confirm whether the tool to be sterilized undergoes steps of the sterilization process, or confirm whether the sterilization is effectively performed, through the change of color tone thereof.

BACKGROUND ART

In the medical institution such as the hospitals, for the purpose of sterilizing tools to be used for surgery or treatment, (1) autoclave sterilization process, (2) ethylene oxide gas sterilization process, or (3) cold plasma sterilization process has been used.

On these sterilization processes, it is important 1) to distinguish whether the tool to be sterilized undergoes the sterilization steps or not; and 2) to detect whether the sterilization effect acting on the tool is proper or not.

Chemical indicators for the sterilization of which color tone are changed when subjected to sterilization have been used as one kind of means for the above mentioned distinguishment or detection, and these indicators should be used for their own specific sterilization method.

(Prior Art of the Indicator for Plasma Sterilization)

The cold plasma sterilization process which utilizes the bactericidal activity of the cold plasma of the oxidizing gas such as hydrogen peroxide gas is suitable for the sterilization of heat-sensitive medical tools, because the cold plasma sterilization process can be performed at a low temperature as in the case of the ethylene oxide gas sterilization process. Further, the cold plasma sterilization process has an advantage that the time required for the sterilization is shorter than the time for the ethylene oxide gas sterilization process.

As the typical cold plasma sterilization process which has been put to practical use until today, the "STERRAD" (registered trademark) which has been developed by Johnson & Johnson Co. (United States). The outline of sterilization step of this sterilization process is as follows, that is, after the inner area of a closed sterilizer is decompressed thoroughly, a constant amount of hydrogen peroxide are injected into the sterilizer and the hydrogen peroxide is allowed to vaporize, then a step where the substance to be sterilized is allowed to contact with the hydrogen peroxide steam for a prescribed time (about 8-16 minutes) and a following step where plasma of the hydrogen peroxide gas is generated by applying high frequency voltage are alternately repeated twice.

We, the inventors, have been already proposed chemical indicators to be used for the cold plasma sterilization process (Patent Literature 1 and Patent Literature 2).

The technological content of the above-mentioned Patent Literature 1 is the one which is related to an indicator which includes a basic dye such as triphenyl methane type, and a compound which has a mercapto group (discoloring assistant), and which is based on a principle that the color of the basic dye is brought into fading as a result of the oxidative decomposition of the basic dye owing to oxidation power of the hydrogen peroxide vapor or of the plasma formed from the hydrogen peroxide vapor.

Further, the content of Patent Literature 2 is the one which is related to an indicator which includes fluorane type colorless dye which has a lactone ring therein and which is used for the thermal recording paper, etc., and a compound which has a dithiocarbamil group (discoloring assistant), and which is based on a principle that the color of the dye is brought into changing as a result of the ring-opening of the lactone ring in the dye to change to a colored rhodamine dye owing to oxidation power of the hydrogen peroxide vapor or of the plasma formed from the hydrogen peroxide vapor.

In addition to the above mentioned indicator, as the indicator to be used for the cold plasma sterilization method, the followings have been also known:

the one which includes an anthraquinone type dye which has an amino group (Patent Literature 3);

the one which includes a pigment which comprises an anthraquinone type compound as a main ingredient and an organic amine type compound (Patent Literature 4);

the one which includes a compound capable of changing its color tone in accordance with the pH variation (Patent Literature 5);

the one which includes a compound selected from the group consisting of adsorption indicators and chelate titration/metal indicators, and an organic metallic compound (Patent Literature 6);

the one which includes a substance of which color is changed by radicals generated when hydrogen peroxide plasma sterilization is performed, such as light green SF yellow, Guinea Green, brilliant green, etc. (Patent Literature 7);

the one which includes (a) adsorption indicator, chelate titration/metal indicator (e.g., hematoxylin, etc.), (b) organic metallic compound, and (c) poly polyhydric alcohol (Patent Literature 8)

the one which includes (a) at least one of anthraquinone type dyes, azo dyes, and methine type dyes; (b) nitrogenous polymer (e.g., polyamide resin, etc.), and (c) cationic surfactant (Patent Literature 9); and the one which includes (a) at least one of styrene-acrylic resins or styrene-maleic resins, and (b) methine type dye (Patent Literature 10).

(Prior Art of the Indicator for Ethylene Oxide Gas Sterilization)

Specific azo dyes used for plasma sterilization according to the present invention are the ones which are known in the art of preparation of indicator for ethylene oxide gas sterilization. As for indicators for ethylene oxide gas sterilization which use such azo dyes, numerous technologies have been already known. Patent Literatures 11-19 may be enumerated as known examples.

In the technology concerning the indicator for the ethylene oxide gas sterilization, the one described in the above mentioned Patent Literature 11 is a principal technique, and the remainder are primarily related to the improving or modifying techniques for the former principal technique.

A viewpoint common to the above mentioned known techniques is that an azo dye which possesses a heterocyclic ring which includes a tertiary nitrogen atom and an appropriate acidic material (decoloring accelerant to promote the reaction of the azo dye and the ethylene oxide) are coated or printed onto a substrate such as paper with the aid of a binder, and the color tone of the obtained indicator is brought into changing to another color tone as a result that the azo dye undergoes an ring-opening addition reaction with ethylene oxide (i.e., ethylene oxide is added to the tertiary nitrogen atom in the heterocyclic ring of the azo dye, and thereby allowing the nitrogen atom to change to quaternary form), and thereby the azo dye is brought into changing to a kind of cationic dye, when the ethylene oxide gas sterilization is performed.

All of the indicators for ethylene oxide gas sterilization which are prepared in accordance with any of the above mentioned techniques hardly discolor upon the cold plasma sterilization process which uses hydrogen peroxide gas or the like.

(Prior Art of the Indicator for Heat Sterilization)

With respect to a specific azo dye which may be used in the indicator for plasma sterilization according to the present invention, an indicator for heat sterilization which is based on a principle that the color of the specific azo dye is brought into changing as a result of reaction of the azo dye with an epoxy compound under the presence of an acidic catalyst has been proposed (Patent Literature 20).

In this indicator, the azo dye and the epoxy compound are mutually separately held in their individual layers via an isolation membrane, and the indicator is based on a principle that its color is changed when the isolation membrane is melted by heat or high pressure steam and thereby the azo dye and the epoxy compound is brought into contacting and reacting with each other.

| [Patent Literature 1] | Japanese Patent No. 3435505 |
| [Patent Literature 2] | Japanese Patent No. 3418937 |
| [Patent Literature 3] | JP 2001 - 174449 A |
| [Patent Literature 4] | JP 2002 - 71570 A |
| [Patent Literature 5] | JP 2002 - 303618 A |
| [Patent Literature 6] | JP 2003 - 102811 A |
| [Patent Literature 7] | JP 2004 - 101488 A |
| [Patent Literature 8] | JP 2004 - 298479 A |
| [Patent Literature 9] | JP 2005 - 315828 A |
| [Patent Literature 10] | JP 2007 - 40785 A |
| [Patent Literature 11] | JP SHO 51 (1976) - 49805 A |
| [Patent Literature 12] | JP SHO 55 (1980) - 69671 A |
| [Patent Literature 13] | JP SHO 56 (1981) - 95053 A |
| [Patent Literature 14] | JP SHO 59 (1984) - 36172 A |
| [Patent Literature 15] | JP SHO 59 (1984) - 219375 A |
| [Patent Literature 16] | JP SHO 62 (1987) - 121777 A |
| [Patent Literature 17] | JP HEI 5 (1993) - 1252 A |
| [Patent Literature 18] | JP 2002 - 294113 A |
| [Patent Literature 19] | JP 2004 - 203984 A |
| [Patent Literature 20] | JP SHO 59 (1984) - 124956 A |

DISCLOSURE OF THE INVENTION

Problem to be Solved by the Invention

The present invention have been done with consideration given to the status quo as mentioned above, and it is principally aimed to provide a novel indicator for plasma sterilization which utilizes an azo dye (an azo dye which possesses a heterocyclic ring which includes a tertiary nitrogen atom) which has been known and used for preparing indicator for ethylene oxide gas sterilization and indicator for heat sterilization, and which exhibits a quick change of color upon the cold plasma sterilization process with using a oxidizing gas such as hydrogen peroxide, the change of color being indicated as a clear change of the color tone, and which also excels in the preservation stability.

Means for Solving the Problem

The indicator for plasma sterilization according to the present invention to solve the above mentioned problem is characterized by comprising:
a) an azo dye represented by the general formula:

(wherein X represents a residue of heterocyclic ring selected from the group consisting of triazole ring, benzothiazole ring, thiadiazole ring, triazole ring, pyridine ring, and quinoline ring, wherein the residue of heterocyclic ring may further optionally include a non-dissociated group as a substituent therein, and Y represents a residue of aniline derivative which is capable of coupling to p-site, wherein the residue of aniline derivative may further optionally include a non-dissociated group as a substituent therein.);
b) a compound containing a mercapto group or a dithiocarbamyl group therein; and
c) a resin as binder.

In the indicator for plasma sterilization according to the present invention, at least one of a polyhydric phenol compound and an aromatic carboxylic acid may be further used as antifading agent for discolored azo dye which is produced during the plasma sterilization process.

Moreover, at least one or more member selected from the group consisting of phenoxy resins, amorphous copolyester resins, polyester-polyurethane resins, polyketone resins, and rosin-modified maleic acid resins may be used as the aforementioned resin as binder.

Alternatively, at least one or more members selected from the group consisting of phenoxy resins, amorphous copolyester resins, polyester-polyurethane resins, polyketone resins, and rosin-modified maleic acid resins; and another resin which has compatibility with the former resin selected from the group may be used as the aforementioned resin as binder, and the using ratio of the former resin and the latter resin may be in the range of 10/90 or more on the basis of weight ratio.

Effect of Invention

As for the indicator for the plasma sterilization according to the present invention, the following effects are achieved.

First, when the indicator is used in an embodiment in which the indicator is coated or printed onto a surface of a packaging material for the sterilization such as a sterilized paper or the like, it becomes possible to confirm whether the object to be sterilized undergoes the sterilization step or not, by color.

Second, when the indicator which is printed on a card or the like undergoes the sterilization process together with the object to be sterilized, it is possible to detect whether the sterilization condition which acted for the object is proper or not after the sterilization was done.

Third, since a clear change of color is given before and after the sterilization and the color tone after the sterilization maintains stably without turning back to the original color tone, it is possible to detect surely the completion of the plasma sterilization treatment.

More concretely, it is as follows.

In the indicator for ethylene oxide gas sterilization or the indicator for heat sterilization, both of which are known in the art, and utilize the same azo dye as the indicator for plasma sterilization according to the present invention utilizes, the discoloring is caused by coming to contact and react the azo dye with an compound which has epoxy group (epoxy ring), i.e., ethylene oxide or epoxy compound, on the sterilization treatment step.

On the other hand, the indicator for plasma sterilization according to the present invention may be prepared by mixing the azo dye with a compound which includes mercapto group(s) therein (or a compound which includes dithiocarbamyl group(s) therein) previously, and then coating them onto a substrate. Under normal preservation condition, the reaction between these two components does not occur even though they are in contact with each other. Therefore, the discoloring is not also caused. When the indicator is subjected to the plasma sterilization condition with using an oxidizing gas such as hydrogen peroxide, however, these two components come to react with each other promptly so as to yield a change in color.

With respect to the indicator for plasma sterilization according to the present invention, in general, a part of discolored azo dye which is produced during the plasma sterilization process tends to be decomposed further by oxidation during the remaining course of the plasma sterilization process, which is followed by the elimination of the color.

It has been found that the degree of decomposition for the discolored azo dye during the sterilization step is also correlated with the kind and adding amount of the compound which includes mercapto group(s) or dithiocarbamyl group(s) therein and which is used in the indicator, as well as the kind of the resin as binder which is used in the indicator.

It is effective to add a polyhydric phenol compound or an aromatic carboxylic acid as a stabilizer against the discolored azo dye in order to prevent the discolored azo dye (a kind of basic dye) which is produced during the plasma sterilization process from causing the decomposition and color-elimination. Thereby, it becomes possible to cause the discoloring phenomenon of the indicator more stable during the sterilization process.

Further, it has been also found that the preservation stability under a high humidity condition for the color tone of the indicator after the plasma sterilization treatment can be enhanced by the kind of the polyhydric phenol compound or the aromatic carboxylic acid when it is selected appropriately.

Incidentally, when an aliphatic carboxylic acid such as malonic acid and maleic acids are used in place of the polyhydric phenol compound or the aromatic carboxylic acid used herein, the effect as mentioned above is hardly obtained.

In the indicator for plasma sterilization according to the present invention, one or more of resins should be used as binder. Depending upon the kind of the resin used, some differences would be seen in the extent of discoloring on the plasma sterilization treatment, the vividness of color tone before and after the sterilization treatment, the extent of stability under a high humidity condition for the color tone after the sterilization treatment, etc.

As a result of the consideration of the resin to be used as the binder, it is found that it may be also possible to use as the binder for the indicator for plasma sterilization of the present invention, an acidic resin such as alkyl phenol resins, rosin modified maleic resins, rosin esters, rosin modified phenolic resins, acrylic copolymers, carboxyl modified vinyl chloride-vinyl acetate copolymers; polyvinyl butyral resins; ethyl celluloses; etc., all of which are generally used in the known indicator for ethylene oxide gas sterilization, singly or in any combination thereof.

Among the above mentioned resins, the rosin modified maleic resin is most preferable from the viewpoint of the extent of discoloring on the plasma sterilization treatment.

In addition to the above mentioned resins, for instance, phenoxy resins, amorphous copolyester resins, solid unsaturated polyester resins, polyester-polyurethane resins, ketone resins, coumarone-indene resins, hydrogenated rosins, etc., may be also utilizable. Particularly, when using phenoxy resin, amorphous copolyester resin, polyester-polyurethane resin, or polyketone resin (particularly, cyclohexanone type), it would be expected that the indicator obtained excels in the discoloring on the plasma sterilization treatment, and the stability under a high humidity condition for the color tone after the sterilization treatment.

BEST MODE FOR CARRYING OUT THE INVENTION

The indicator for plasma sterilization according to the present invention may be manufactured by:
dissolving a) a specific azo dye represented by the general formula: X—N=N—Y; b) a compound containing a mercapto group or a dithiocarbamyl group therein as a component which is able to react with the azo dye upon the plasma sterilization treatment, and thereby, to bring discoloring into the azo dye; and c) a resin as binder; wherein all of the above a), b), c) components are added as essential components; and optionally d) a polyhydric phenol compound or an aromatic carboxylic acid, which functions to enhance the stability of molecules of azo dyes after discoloring, as an optional component; into a ketone type solvent or other solvent to prepare an ink; and printing or coating the obtained ink with an appropriate thickness to a substrate such as polyethylene type or polypropylene type nonwaven fabric or film which is low in absorbency to the hydrogen peroxide or the like which is used for the sterilization.

Because the mixing ratio of these components may be varied in accordance with the depth of color of the azo dye used; the kind of the reactive component, i.e., the compound containing a mercapto group or the compound containing a dithiocarbamyl group therein; the kind of the polyhydric phenol compound or the aromatic carboxylic acid; as well as viscosity obtained when the resin as binder is dissolved into the solvent; and adhesiveness of the ink coating to the substrate, it may be adjusted properly.

Moreover, in addition to the above mentioned essential components, it may be possible to add optionally a dye or pigment which can not be discolored by the plasma sterilization treatment, and/or an ultraviolet absorbing agent, if necessary.

With respect to the specific azo dyes to be used for the indicator for plasma sterilization according to the present invention, they are known in the techniques for preparing the indicator for ethylene oxide gas sterilization or the indicator for heat sterilization. For instance, those which are disclosed in Patent Literature 15, 20, etc., and represented as follows may be used.

Namely, the azo dyes represented by the general formula:

(wherein X represents a residue of heterocyclic ring selected from the group consisting of triazole ring, benzothiazole ring, thiadiazole ring, triazole ring, pyridine ring, and quinoline ring, wherein the residue of heterocyclic ring may further optionally include a non-dissociated group as a substituent therein, and Y represents a residue of aniline derivative which is capable of coupling to p-site, wherein the residue of aniline derivative may further optionally include a non-dissociated group as a substituent therein.) are enumerated, and at least one of them is use.

As the compound containing a mercapto group therein which may be used in the indicator for plasma sterilization according to the present invention, for instance, 2-mercapto benzothiazole, 6-ethyl-2-mercapto benzothiazole, 6-ethoxy-2-mercapto benzothiazole, 2-mercapto thiazoline, 5-methyl-1,3,4-thiadiazole-2-thiol, 1-phenyl-5-mercapto-1H-tetrazole, 4,4'-thiobisbenzenethiol, 2-mercapto-5-methoxy-benzoimidazole, 2-mercapto-5-methyl-benzoimidazole, 2-mercapto-5-methoxy-benzoimidazole, 2-mercapto-5-ethoxy-benzoimidazole, 2-mercapto-nicotinic acid, etc., are exemplified.

As the compound containing a dithiocarbamyl group therein which may be used in the indicator for plasma sterilization according to the present invention, for instance, tetramethyl thiuram monosulfide, tetramethyl thiuramdisulfide, tetraethyl thiuramdisulfide, tetrabuthyl thiuram disulfide, dipentamethylene thiuram tetrasulfide, tetramethyl thiuramdisulfide, tetrabenzyl thiuramdisulfide, 2-benzothiazolyl diethyldithiocarbamate, etc., are exemplified.

Among the compounds each containing a dithiocarbamyl group therein as mentioned above, tetramethyl thiuram disulfide, and tetraethyl thiuram disulfide are desirable because an indicator of being prompt in discoloring on the plasma sterilization treatment will be obtained.

However, with respect to the compound containing a dithiocarbamyl group therein, in general, there is a defect that the range of optimum addition amounts is considerably narrow as compared with that of the compound containing a mercapto group therein.

In the indicator for plasma sterilization according to the present invention, at least one of a polyhydric phenol compound and an aromatic carboxylic acid may be further used, in order to prevent a part of the discolored azo dye which is produced during the plasma sterilization process from causing the color-elimination due to its oxidation during the remaining course of the plasma sterilization process and to stabilize the discoloration stable.

As effective polyhydric phenol compounds, 2,2-bis(4-hydroxy phenyl)propane, 2,2-bis(4-hydroxy phenyl)hexafluoro propane, 2,2-bis(4-hydroxy phenyl)butane, 2,2-bis(4-hydroxy-3-methyl phenyl)propane, 2,2-bis(3-sec-butyl-4-hydroxy phenyl)propane, 4,4'-butylidene bis(6-tert-butyl-m-cresol), 2,2-bis(2-hydroxy-5-biphenyl)propane, 2,2-bis(3-cyclohexyl-4-hydroxy phenyl)propane, 4,4'-(α-methyl benzylidene)bisphenol, 4,4'-dihydroxy tetraphenyl methane, α,α'-bis(4-hydroxy phenyl)-1,4-diisopropyl benzene, 1,3-bis(4-hydroxy phenoxy)benzene, 1,4-bis(3-hydroxy phenoxy)benzene, bis(4-hydroxy phenyl)sulfone, bis(4-hydroxy phenyl)sulfide, bis(4-hydroxy-3-methyl phenyl)sulfide, 4,4'-thiobis(6-tert-butyl-m-cresol), 2,2'-thiobis(4-tert-octyl phenol), 1,1'-thiobis(2-naphthol), bis(6-hydroxy-2-naphtyl)disulfide, 1,1-bis(4-hydroxy-3-methyl phenyl)cyclohexane, 1,1-bis(3-cyclohexyl-4-hydroxy phenyl)cyclohexane, 9,9-bis(4-hydroxy phenyl)fluorene, 9,9-bis(4-hydroxy-3-methyl phenyl)fluorene, 1,1-bis(4-hydroxy phenyl)cyclohexane, 1,5-dihydroxy naphthalene, 2,3-dihydroxynaphthalene, 2,2'-dihydroxy-4,4'-dimethoxy benzophenone, 4,4'-dihydroxy benzophenone, 2,2',4,4'-tetrahydroxy benzophenone, 2,2'-methylene bis(4-chloro phenol), 2-[bis(4-hydroxy phenyl)methyl]benzyl alcohol, 1,1'-methylene di-2-naphthol, 1,3-bis[2-(4-hydroxy phenyl)-2-propyl]benzene, 4,4',4''-trihydroxy triphenyl methane, 1,1,1-tris(4-hydroxy phenyl)ethane, 2,6-bis[(2-hydroxy-5-methyl phenyl)methyl]-4-methyl phenol, α,α,α'-tris(4-hydroxy phenyl)-1-ethyl-4-isopropyl benzene, 2,2',3,3'-tetrahydroxy-1,1'-binaphthyl, diphenolic acid, phenolphthalin, methylene disalicylate, etc., may be enumerated.

As the polyhydric phenol compounds, in general, those which have a high acid strength are effective. Further, among them, those which possess low hydrophilicity are useful for providing the stability under a high humidity condition for the color tone of the indicator after the plasma sterilization treatment.

Moreover, it is also important to choose and to use a polyhydric phenol compound which shows a good compatibility to the resin as the binder to be used, since it is preferable that the polyhydric phenol compound is used in a high addition amount of about 10-100% by weight on the basis of the addition amount of the resin as binder to be used in the indicator.

As effective aromatic carboxyl acids, for instance, 2-naphthonic acid, 2-hydryoxy-3-aphthonic acid, 3,5-di-tert-butyl salicylic acid, p-tolyl-o-benzoic acid, o-phthalic acid, etc., may be exemplified.

In the indicator for plasma sterilization according to the present invention, one or more of resins should be used as binder. As mentioned above, the kind of the resin used influences to the extent of discoloring on the plasma sterilization treatment, the vividness of color tone before and after the sterilization treatment, the extent of stability under a high humidity condition for the color tone after the sterilization treatment, or the like.

As the binder which is particularly suitable for using in the indicator for plasma sterilization method according to the present invention, it is found that there are phenoxy resins, amorphous copolyester resins, polyester-polyurethane resins, and polyketone resins (particularly, cyclohexanone type), as well as the rosin modified maleic resins which are used in the known indicator for ethylene oxide gas sterilization. When these resins are used singly or in combination, it is expected to obtain a good result. Further, it is also possible to use any of these resins in combination with other resin which has compatibility with the former resin(s). In such a case, it is necessary that the using ratio of the former resin and the latter resin is in the range of 10/90 or more on the basis of weight ratio, although it would be varied by the kinds of resins used and the purpose of the combination use.

As the phenoxy resin used as the binder of the indicator for plasma sterilization according to the present invention, the one which has completely no epoxy group is particularly preferable.

In general, the epoxy resin which is liner and has a high polymerization degree is referred to as phenoxy resin. Although it has epoxy groups at the terminal ends of the molecular chain, the amount of the epoxy groups contained therein is relatively low because of its high polymerization degree. Notwithstanding the above fact, as the phenoxy resin to be used as binder of the indicator for plasma sterilization according to the present invention, the one of which epoxy groups existing at the terminal ends of the molecular chain have been forced to be opened and disappeared, and thus which has no epoxy group is further preferable (This is because the epoxy groups may react with the azo dye during storage, and which is followed by the occurrence of discoloration in some degree).

EXAMPLE

Now, the present invention will be described concretely by the following examples.

Examples 1 and 2

(a) As azo dye: C.I Disperse Red 58, 20 mg
(b) As reactive substance: 5-methyl-1,3,4-thiadiazole-2-thiol, 50 mg
(c) As polyhydric phenol compound: none for Example 1; 4,4'-(α-methyl benzylidene)bisphenol, 200 mg for Example 2
(d) As binder (resin): amorphous copolyester resin (VYLON® 240, manufactured by Toyobo Co., Ltd.), 10000 mg
(e) As solvent: methyl ethyl ketone, 20 mL Inks were prepared respectively with the above components. Each ink was hand coated with a wire bar in 0.6 m/m onto an individual polypropylene type synthetic paper (YUPO FGS-250, manufactured by YUPO Corporation) substrate in order to produce indicators for plasma sterilization of Examples 1 and 2.

Both of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 1.

Herein, the "2 minutes canceling treatment" in the table denotes the treatment where the sterilization chamber is decompressed to approximately 0.5 Torr; then, the high frequency energy is applied in the sterilization chamber while maintaining the reduced pressure condition in order to generate air plasmatic condition; next, the chamber is once allowed to restore pressure, then, the chamber is again decompressed to approximately 0.5 Torr; and then, hydrogen peroxide is supplied to the chamber and allowed to disperse in the chamber for 2 minutes.

The "short cycle treatment" denotes the treatment where the above mentioned "2 minutes canceling treatment" is followed by allowing hydrogen oxide to disperse in the chamber for another 6 minutes, decompressing slightly, applying the high frequency energy in the sterilization chamber in order to generate cold plasmatic condition of hydrogen peroxide; then further supplying hydrogen peroxide; allowing hydrogen oxide to disperse in the chamber for further another 8 minutes; and further applying the high frequency energy.

These terms will be used hereinafter in the same meaning.

TABLE 1

|  | 2 minutes canceling treatment | Short cycle treatment |
| --- | --- | --- |
| Example 1 | Purple | Blue |
| Example 2 | Blue | Blue - Sky blue |

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 2.

TABLE 2

|  | Test result for 2 minutes canceling treated article | Test result for short cycle treated article |
| --- | --- | --- |
| Example 1 | Nominal turn-back of color | Nominal turn-back of color |
| Example 2 | Substantially no change | Substantially no change |

(Controls 1 and 2)

For making a comparison with Examples 1 and 2, inks were prepared in the same fashion as Examples 1 and 2 except for the reactive substance (5-methyl-1,3,4-thiadiazole-2-thiol) was omitted from the ink component (Controls 1 and 2). Then, the obtained inks underwent the sterilization treatment in the plasma sterilizer from Johnson & Johnson Co. in the same fashion as Examples 1 and 2. As the result, neither of the samples of Controls 1 and 2 were discolored at all, and they were still in red as is before treatment.

Examples 3 and 4

(a) As azo dye: C.I Disperse Red 58, 20 mg
(b) As reactive substance: 2-mercapto benzothiazole, 100 mg
(c) As polyhydric phenol compound: none for Example 3; 1,1-bis(hydroxy phenyl)cyclohexane, 1800 mg for Example 4
(d) As binder (resin): phenoxy resin (PKHC, manufactured by Union Carbide Corporation, USA), 8000 mg
(e) As solvent: methyl ethyl ketone, 27 mL Inks were prepared respectively with the above components. Each ink was hand coated with a wire bar in 0.6 m/m onto an individual polypropylene type synthetic paper (YUPO FGS-250, manufactured by YUPO Corporation) substrate in order to produce indicators for plasma sterilization of Examples 3 and 4.

Both of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 3.

TABLE 3

|  | 2 minutes canceling treatment | Short cycle treatment |
| --- | --- | --- |
| Example 3 | Purple | Blue |
| Example 4 | Purple | Blue - Sky blue |

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 4.

TABLE 4

|  | Test result for 2 minutes canceling treated article | Test result for short cycle treated article |
| --- | --- | --- |
| Example 3 | Slight turn-back of color | Slight turn-back of color |
| Example 4 | Substantially no change | Substantially no change |

Examples 5 and 6

(a) As azo dye: C.I Disperse Red 58, 20 mg
(b) As reactive substance: 2-mercapto benzothiazole, 50 mg
(c) As polyhydric phenol compound: none for Example 5; 1,1'-thiobis (2-naphthol), 1800 mg for Example 6
(d) As binder (resin): polyester—polyurethane resin solution (VYLON® UR-4800 (32 wt. % solution), manufactured by Toyobo Co., Ltd.), 20000 mg
(e) As supplemental solvent: methyl ethyl ketone, 9 mL Inks were prepared respectively with the above components. Each ink was hand coated with a wire bar in 0.6 m/m onto an individual polypropylene type synthetic paper (YUPO FGS-250, manufactured by YUPO Corporation) substrate in order to produce indicators for plasma sterilization of Examples 5 and 6.

Both of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 5.

TABLE 5

|  | 2 minutes canceling treatment | Short cycle treatment |
| --- | --- | --- |
| Example 5 | Violet red | Blue |
| Example 6 | Blue violet | Blue - Sky blue |

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 6.

TABLE 6

|  | Test result for 2 minutes canceling treated article | Test result for short cycle treated article |
| --- | --- | --- |
| Example 5 | Substantially no change | Substantially no change |
| Example 6 | No change | No change |

Examples 7-11

(a) As azo dye: C.I Disperse Red 58, 20 mg
(b) As reactive substance: 5-methyl-1,3,4-thiadiazole-2-thiol, 30 mg
(c) As polyhydric phenol compound: none for Example 7; 2,2-bis(4-hydroxy phenyl)propane [Bisphenol A], 150 mg, for Example 8; 1,1-bis(4-hydroxy phenyl)cyclohexane [Bisphenol Z], 150 mg, for Example 9; bis(4-hydroxy phenyl)sulfone [Bisphenol S], 150 mg, for Example 10; 4,4'-(α-methyl benzylidene)bisphenol [Bisphenol AP], 150 mg, for Example 11;
(d) As binder (resin): amorphous copolyester resin (VYLON® 240, manufactured by Toyobo Co., Ltd.), 5000 mg
(e) As solvent: methyl ethyl ketone, 15 mL Inks were prepared respectively with the above components. Each ink was hand coated with a wire bar in 0.6 m/m onto an individual polypropylene type synthetic paper (YUPO FGS-250, manufactured by YUPO Corporation) substrate in order to produce indicators for plasma sterilization of Examples 7-11.

All of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 7.

TABLE 7

|  | 2 minutes canceling treatment | Short cycle treatment |
| --- | --- | --- |
| Example 7 | Purple | Blue violet |
| Example 8 | Blue violet | Blue |
| Example 9 | Blue violet | Blue |
| Example 10 | Blue violet | Blue |
| Example 11 | Blue violet | Blue |

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 8.

TABLE 8

|  | Test result for 2 minutes canceling treated article | Test result for short cycle treated article |
| --- | --- | --- |
| Example 7 | Turn-back of color to a certain degree(Somewhat reddish violet) | Turn-back of color to a certain degree (Bluish violet) |
| Example 8 | Considerable turn-back of color (Violet red - Red) | Considerable turn-back of color (Violet red) |
| Example 9 | No change (Blue violet) | No change (Blue) |
| Example 10 | Considerable turn-back of color (Violet red - Red)) | Considerable turn-back of color (Violet red) |
| Example 11 | No change (Blue violet) | No change (Blue) |

All of four kinds of polyhydric phenol compounds used for the indicator of Examples 8-11 have high acid strengths. When adding such a polyhydric phenol compound of high acid strength, the extent of discoloration of the indicator upon the plasma sterilization could be improved (This is because the blue azo dye caused at the sterilization treatment step is brought into a stability, and thus it becomes difficult to receive oxidative decomposition during the remaining course of the sterilization treatment step. With respect to the extent of stability under a high humidity condition for the color tone after the sterilization treatment, however, it is affected by the hydrophilic property of the polyhydric phenol compound added. Therefore, the indicators of Examples 9 and 11 in which Bisphenol Z and Bisphenol AP, both of which have a low hydrophilic property, were added, respectively, shown an enhanced moisture resistance; whereas the indicators of Examples 8 and 10 in which Bisphenol A and Bisphenol S, both of which have a high hydrophilic property, were added, respectively, showed an moisture resistance after sterilization treatment of a degraded level rather than improved.

Examples 12 and 13

(a) As azo dye: C.I Disperse Red 58, 20 mg
(b) As reactive substance: 2-mercapto benzothiazole, 30 mg
(c) As polyhydric phenol compound: none for Example 12; 1,1-bis(4-hydroxy phenyl)cyclohexane, 1800 mg for Example 13
(d) As binder (resin): rosin modified maleic resin (Tespol 1152, manufactured by Hitachi Kasei Polymer Co., Ltd.), 16000 mg
(e) As solvent: methyl ethyl ketone, 13 mL Inks were prepared respectively with the above components. Each ink was hand coated with a wire bar in 0.45 m/m onto an individual polypropylene type synthetic paper (YUPO FGS-250, manufactured by YUPO Corporation) substrate in order to produce indicators for plasma sterilization of Examples 12 and 13.

Both of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 9.

TABLE 9

|  | 2 minutes canceling treatment | Short cycle treatment |
| --- | --- | --- |
| Example 12 | Blue (slightly tinged with violet) | Blue - Sky blue |
| Example 13 | Blue (very slightly tinged with violet) | Blue - Sky blue |

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 10.

TABLE 10

|  | Test result for 2 minutes canceling treated article | Test result for short cycle treated article |
|---|---|---|
| Example 12 | Considerable turn-back of color (Violet red) | Considerable turn-back of color (Violet red) |
| Example 13 | Considerable turn-back of color (Reddish violet) | Considerable turn-back of color (Reddish violet) |

As shown in Examples 12 and 13 as above mentioned, in general, the indicator for plasma sterilization in which the rosin modified maleic resin is used as binder has characteristics that it excels in the extent of the discoloration on the plasma sterilization treatment, and also in the vividness of color tone after the sterilization treatment, but it is slightly inferior in the extent of stability under a high humidity condition for the color tone after the sterilization treatment.

However, when the test was carried out under the condition of 23° C., 60% RH instead of the condition of 23° C., 90% RH for 1 month, it was found that the change of color tone was little even after 3 months, especially, in Example 13, the change of color tone hardly took place.

Examples 14 and 15

(a) As azo dye: C.I Disperse Red 58, 20 mg
(b) As reactive substance: tetraethyl thiuram disulfide, 15 mg
(c) As polyhydric phenol compound: none for Example 14; 4,4'-(α-methyl benzylidene)bisphenol, 1800 mg for Example 15
(d) As binder (resin): amorphous copolyester resin (VYLON® 240, manufactured by Toyobo Co., Ltd.), 10000 mg, 20000 mg
(e) As solvent: methyl ethyl ketone, 20 mL Inks were prepared respectively with the above components. Each ink was hand coated with a wire bar in 0.45 m/m onto an individual polypropylene type synthetic paper (YUPO FGS-250, manufactured by YUPO Corporation) substrate in order to produce indicators for plasma sterilization of Examples 14 and 15.

Both of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 11.

TABLE 11

|  | 2 minutes canceling treatment | Short cycle treatment |
|---|---|---|
| Example 1 | Substantially no change (Red) | Purple |
| Example 2 | Bluish Violet | Blue |

When the polyhydric phenol compound was not added as in Example 14, the discoloration upon the sterilization treatment was very late (from the result of color tone on 2 minutes canceling treatment). This case indicates that the fading which is brought by the oxidative decomposition of the blue azo dye caused at the sterilization step progresses at very fast rate. Even if the addition amount of the reactive substance, tetraethyl thiuram disulfide, is increased in such a composition, the extent of discoloring on 2 minutes canceling treatment is not very improved When the polyhydric phenol compound was added as in Example 15, the indicator discolored on the 2 minutes canceling treatment and the short cycle treatment. Even in this composition, however, when the addition amount of the reactive substance, tetraethyl thiuram disulfide, was increased too much, the depth of blue color on the short cycle treatment became low (it was considered that it is because a part of the once caused blue azo dye would fade.).

Further, for investigating the stability under a high humidity condition for the sterilization treatment experienced indicator, a test was carried out where the specimen after sterilization was left standing in a thermo-hygrostat set at 23° C., 90% RH for 1 month. As a result, it was found that both of the indicator which underwent 2 minutes canceling treatment and the indicator which underwent short cycle treatment were not substantially changed in color, and thus had a good moisture resistance.

Examples 16-18

(a) As azo dye: C.I Disperse Red 58, 20 mg
(b) As reactive substance: 2-mercaptobenzothiazole, 100 mg, 200 mg, 300 mg, for Example 16, 17, 18, respectively
(c) As polyhydric phenol compound: 1,1-bis(4-hydroxyphenyl)cyclohexane, 2000 mg
(d) As binder (resin): phenoxy resin (PKHC, manufactured by Union Carbide Corporation, USA), 2000 mg, and acetophenone type ketone resin (HALON 80, manufactured by Honshu Chemical Industry Co., Ltd.), 8000 mg for Example 16;

phenoxy resin (PKHC, manufactured by Union Carbide Corporation, USA), 2000 mg, and hydrogenated acetophenone type ketone resin (HALON 110H, manufactured by Honshu Chemical Industry Co., Ltd.), 8000 mg for Example 17 phenoxy resin (PKHC, manufactured by Union Carbide Corporation, USA), 2000 mg, and cyclohexanone type ketone resin (Ketone resin K-90, manufactured by Arakawa Chemical Industries, Ltd.), 8000 mg for Example 18

(e) As solvent: methyl ethyl ketone, 10 mL, 11 mL, 11 mL, for Example 16, 17, 18, respectively Inks were prepared respectively with the above components. Each ink was hand coated with a wire bar in 0.45 m/m onto an individual polypropylene type synthetic paper (YUPO FGS-250, manufactured by YUPO Corporation) substrate in order to produce indicators for plasma sterilization of Examples 16-18.

Incidentally, in the indicators of these examples, although the ketone resin was mainly used as binder, the reason for using a small amount of phenoxy resin together with the ketone resin was to enhance the strength of the binder.

All of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 12.

TABLE 12

|  | 2 minutes canceling treatment | Short cycle treatment |
| --- | --- | --- |
| Example 16 | Blue (tinged with violet to a certain degree) | Blue |
| Example 17 | Blue violet | Blue |
| Example 18 | Purple | Blue |

In general, the discoloration of the indicator that uses the ketone resin as a binder upon the plasma sterilization was excellent.

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 13.

TABLE 13

|  | Test result for 2 minutes canceling treated article | Test result for short cycle treated article |
| --- | --- | --- |
| Example 16 | Turn-back of color to a certain degree (Bluish violet) | Turn-back of color to a certain degree (Bluish violet) |
| Example 17 | Turn-back of color to a certain degree (Purple) | Turn-back of color to a certain degree (Bluish violet) |
| Example 18 | Substantially no change (Purple) | Substantially no change (Blue) |

The indicator which used the cyclohexanone type ketone resin as binder also excelled in the stability under a high humidity condition for the color tone after the plasma sterilization treatment.

Examples 19-24

(a) As azo dye: C.I Disperse Red 58, 20 mg
(b) As reactive substance: 2-mercaptobenzothiazole, 100 mg,
(c) As acidic substance: none for Example 19; malonic acid which is an aliphatic carboxylic acid, 40 mg (Because of its high acid strength, it is not possible to increase the addition amount any more.), for Example 20; maleic acid which is an aliphatic carboxylic acid, 20 mg (Because of its high acid strength, it is not possible to increase the addition amount any more.), for Example 21; p-tolyl-o-benzoic acid which is an aromatic carboxylic acid, 1500 mg, for Example 22; 2-naphthonic acid which is an aromatic carboxylic acid, 800 mg, for Example 23; 4,4'-(α-methyl benzylidene)bisphenol which is a polyhydric phenol compound, 1500 mg, for Example 24
(d) As binder (resin): the used was a blend that included cumarone resin as main ingredient, and a small amount of amorphous copolyester resin, wherein the amorphous copolyester resin were added for the purpose of compensating for the strength as the binder. Concretely, amorphous copolyester resin (VYLON® 240, manufactured by Toyobo Co., Ltd.), 1500 mg and cumarone resin (Escron V-120, manufactured by Nitto Chemical Co., Ltd.) 6000 mg
(e) As solvent: methyl ethyl ketone, 10 mL Inks were prepared respectively with the above components. Each ink was hand coated with a wire bar in 0.45 m/m onto an individual polypropylene type synthetic paper (YUPO FGS-250, manufactured by YUPO Corporation) substrate in order to produce indicators for plasma sterilization of Examples 19-24.

All of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 14.

TABLE 14

|  | 2 minutes canceling treatment | Short cycle treatment |
| --- | --- | --- |
| Example 19 | Violet red | Dark violet |
| Example 20 | Violet red | Dark violet |
| Example 21 | Violet red | Dark violet |
| Example 22 | Purple | Medium slate blue |
| Example 23 | Violet red | Medium purple |
| Example 24 | Bluish violet | Blue |

When an indicator which used cumarone resin as binder was prepared without acidic substance, the indicator was inferior in the extent of discoloration upon the plasma sterilization treatment as shown in Example 19 (This would be probably because apart of blue azo dye which caused during the plasma sterilization treatment underwent oxidative decomposition during the rest course of the plasma sterilization treatment, and thus shown a tendency of easy fading.).

Incidentally, the reason why the indicator discolored to such color tones having a grayish tinge upon the short cycle treatment was considered as follows. That is, although the indicator turned to purple upon the short cycle treatment, the slightly yellowish color due to the cumarone resin would be added to the purple color because the discoloration upon the sterilization is slow as described above, and thus the purple (or violet) having a grayish tinge was formed.

When various acidic substances were added individually to this type indicator, a difference on the extent of discoloration upon the plasma sterilization would arise according to the kind of the acidic substance added.

With respect to the relation between the kind of the acidic substance and the improving effect on the extent of discoloration upon the plasma sterilization treatment, it was found that substantially no effect was obtained by adding an aliphatic carboxylic acid (Examples 20 and 21), a slight effect was obtained by adding an aromatic carboxylic acid (Examples 22 and 23), and an evident effect was obtained by adding a polyhydric phenol compound (Example 24).

For investigating the stability under a high humidity condition for the color tone of the sterilization treatment experienced indicator of Example 24 which shown an excellent extent of discoloration upon the plasma sterilization treatment among the above mentioned examples, a test was carried out where the specimen after sterilization was left standing in a thermo-hygrostat set at 23° C., 90% RH for 1 month. As a result, it was found that both of the indicator which underwent 2 minutes canceling treatment and the indicator which underwent short cycle treatment were not substantially changed in color, and thus had a almost good stability under a high humidity condition after the sterilization treatment.

Examples 25-33

(a) As azo dye: C.I Disperse Red 58, 20 mg
(b) As reactive substance: 2-mercaptobenzothiazole, 150 mg,
(c) As acidic substance: none for Example 25; maleic acid which is an aliphatic carboxylic acid, 40 mg (Because of its high acid strength, it is not possible to increase the addition amount any more.), for Example 26; p-tolyl-o-benzoic acid which is an aromatic carboxylic acid, 1500 mg, for Example 27; 2-naphthonic acid which is an aromatic carboxylic acid, 1000 mg, for Example 28; 3,5-di-tert-butyl salicylic acid which is an aromatic carboxylic acid, 1000 mg, for Example 29; diphenolic acid which is an polyhydric phenol compound, 1000 mg, for Example 30; phenolphthalein which is an polyhydric phenol compound, 1500 mg, for Example 31; methylene disalicylate which is an polyhydric phenol compound, 1000 mg, for Example 32; 1,1-bis(4-hydroxy phenyl)cyclohexane which is a polyhydric phenol compound, 1500 mg, for Example 33

(d) As binder (resin): amorphous copolyester resin (VYLON® 240, manufactured by Toyobo Co., Ltd.), 2000 mg and hydrogenated rosin resin(hydrogenated rosin, manufactured by Arakawa Chemical Industries, Ltd.) 8000 mg (e) As solvent: methyl ethyl ketone, 10 mL Inks were prepared respectively with the above components. Each ink was hand coated with a wire bar in 0.45 m/m onto an individual polypropylene type synthetic paper (YUPO FGS-250, manufactured by YUPO Corporation) substrate in order to produce indicators for plasma sterilization of Examples 25-33.

All of these indicators showed almost red. These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 15.

TABLE 15

|  | 2 minutes canceling treatment | Short cycle treatment |
|---|---|---|
| Example 25 | Somewhat bluish violet | Light navy |
| Example 26 | " | " |
| Example 27 | " | Somewhat lighter navy |
| Example 28 | " | " |
| Example 29 | " | " |
| Example 30 | Bluish violet | Blue(tinged with navy to a certain degree) |
| Example 31 | " | Blue(tinged with navy to a certain degree) |
| Example 32 | " | Blue(tinged with navy to a certain degree) |
| Example 33 | " | Blue(tinged with navy to a certain degree) |

In the indicators of examples 25-33, the used as binder was a blend that included hydrogenated rosin as main ingredient, and a small amount of amorphous copolyester resin, wherein the amorphous copolyester resin were added for the purpose of compensating for the strength as the binder.

With respect to the indicator prepared without acidic substance (Example 25), it was found that the discoloration upon the plasma sterilization was to change to light navy, but not to blue, for the short cycle treatment.

The reason why discoloring to such a color tone was considered as follows. That is, apart of blue azo dye which caused during the plasma sterilization treatment would undergo oxidative decomposition during the rest course of the plasma sterilization treatment, and thereby the color would fade to light blue color, and the light yellow color due to the hydrogenated rosin would be added to the light blue color.

With respect to the relation between the kind of the acidic substance added and the improving effect on the extent of discoloration upon the plasma sterilization treatment, it was found that substantially no effect was obtained by adding an aliphatic carboxylic acid (Example 26), a slight effect was obtained by adding an aromatic carboxylic acid (Examples 27-29), and an evident effect was obtained by adding a polyhydric phenol compound (Examples 30-33), as shown in above table.

For investigating the stability under a high humidity condition for the color tone of the sterilization treatment experienced indicator, a test was carried out where the specimen after sterilization was left standing in a thermo-hygrostat set at 23° C., 90% RH for 1 month. The obtained results were as shown in Table 16.

TABLE 16

|  | Test result for 2 minutes canceling treated article | Test result for short cycle treated article |
|---|---|---|
| Example 25 | Turn-back of color to a certain degree(Reddish tinge increased to a certain degree.) | Slight turn-back of color |
| Example 26 | Turn-back of color to a certain degree(Reddish tinge increased to a certain degree.) | " |
| Example 27 | Slight turn-back of color (Reddish tinge increased slightly.) | " |
| Example 28 | Slight turn-back of color (Reddish tinge increased slightly.) | " |
| Example 29 | Slight turn-back of color (Reddish tinge increased slightly.) | " |
| Example 30 | Slight turn-back of color (Reddish tinge increased slightly.) | " |
| Example 31 | Slight turn-back of color (Reddish tinge increased slightly.) | " |
| Example 32 | Slight turn-back of color (Reddish tinge increased slightly.) | " |
| Example 33 | Nominal turn-back of color | Nominal turn-back of color |

Examples 34-38

(a) As azo dye: compound represented by the following chemical formula (1), 20 mg, for Example 34; compound represented by the following chemical formula (2), 20 mg, for Example 35; compound represented by the following chemical formula (3), 20 mg, for Example 36; compound represented by the following chemical formula (4), 20 mg, for Example 37; compound represented by the following chemical formula (5), 20 mg, for Example 38

[Chemical 1]

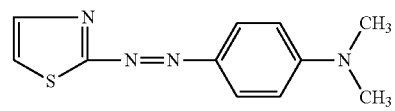

(1)

[Chemical 2]

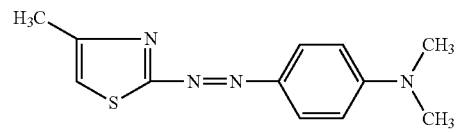

(2)

-continued

[Chemical 3]

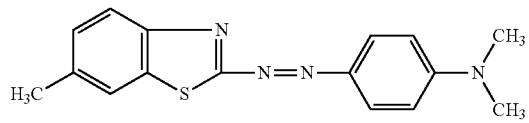
(3)

[Chemical 4]

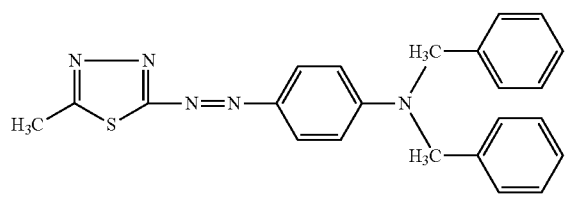
(4)

[Chemical 5]

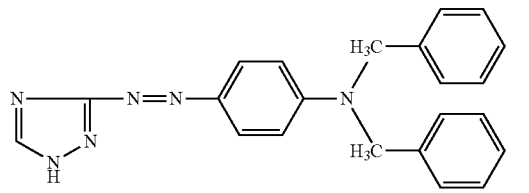
(5)

(b) As reactive substance: 2-mercapto benzothiazole, 50 mg, 50 mg, 50 mg, 100 mg, 25 mg, for Examples 34, 35, 36, 37, 38, respectively (c) As polyhydric phenol compound: 1,1'-bis(4-hydroxy phenyl)cyclohexane, 1500 mg (d) As binder (resin): polyester-polyurethane resin solution (VYLON® UR-4800, manufactured by Toyobo Co., Ltd.), 3.9 mL (3.7 g)

(e) As supplemental solvent: methyl ethyl ketone, 7.7 mL

Inks were prepared respectively with the above components. Each ink was hand coated with a wire bar in 0.35 m/m onto an individual polypropylene type synthetic paper (YUPO FGS-250, manufactured by YUPO Corporation) substrate in order to produce indicators for plasma sterilization of Examples 34-38.

These indicators underwent sterilization treatment (2 minutes canceling treatment or short-cycle treatment) in the plasma sterilizer (STERRAD 100S) commercially available from Johnson & Johnson Co. After the sterilization treatment, the indicators discolored as shown in Table 17.

TABLE 17

|  | Before sterilization | 2 minutes canceling treatment | Short cycle treatment |
|---|---|---|---|
| Example 34 | Red | Violet red | Purple |
| Example 35 | Red | Reddish violet | Bluish violet |
| Example 36 | Red | Purple | Bluish violet |
| Example 37 | Orange | Deep pink | Pink |
| Example 38 | Yellow | Orange | Orange red |

For investigating the stability under a high humidity condition for the color tone of the sterilization treatment experienced indicator, a test was carried out where the specimen after sterilization was left standing in a thermo-hygrostat set at 23° C., 90% RH for 1 month. As a result, it was found that substantially no change of color tone was caused on the specimen of each example, and thus the indicators of these examples had excellent stability under a high humidity condition after the sterilization treatment.

The invention claimed is:

1. An indicator for plasma sterilization comprising:
a) an azo dye represented by the general formula:

X—N=N—Y, wherein X represents a residue of heterocyclic ring selected from the group consisting of triazole ring, benzothiazole ring, thiadiazole ring, triazole ring, pyridine ring, and quinoline ring, wherein the residue of heterocyclic ring may further optionally include a non-dissociated group as a substituent therein, and Y represents a residue of aniline derivative of which p-site is capable of coupling to a neighboring N atom, wherein the residue of aniline derivative may further optionally include a non-dissociated group as a substituent therein;
b) a compound containing a mercapto group or a dithiocarbamyl group therein; and
c) a resin as binder, wherein the binder is at least one or more members selected from the group consisting of phenoxy resins, amorphous copolyester resins, polyester-polyurethane resins, and cyclohexanone type polyketone resins.

2. The indicator for plasma sterilization according to claim 1, wherein at least one of a polyhydric phenol compound and an aromatic carboxylic acid is further used as antifading agent for discolored azo dye which is produced during the plasma sterilization process.

3. The indicator for plasma sterilization according to claim 1, wherein the resin as binder is at least one or more members selected from the group consisting of phenoxy resins, amorphous copolyester resins, polyester-polyurethane resins, and cyclohexanone type polyketone resins, and another resin which has compatibility with the former resin selected from the group, and the using ratio of the former resin and the latter resin is in the range of 10/90 or more on the basis of weight ratio.

4. The indicator for plasma sterilization according to claim 2, wherein the resin as binder is at least one or more members selected from the group consisting of phenoxy resins, amorphous copolyester resins, polyester-polyurethane resins, and cyclohexanone type polyketone resins, and another resin which has compatibility with the former resin selected from the group, and the using ratio of the former resin and the latter resin is in the range of 10/90 or more on the basis of weight ratio.

5. The indicator for plasma sterilization according to claim 1, wherein the azo dye and the compound containing the mercapto group or the dithiocarbamyl group therein are capable of reacting with each other so as to yield a change in color when the indicator is subjected to the plasma sterilization condition with using an oxidizing gas, and the azo dye and the compound containing the mercapto group or the dithiocarbamyl group therein are not capable reacting with each other under normal preservation condition.

6. The indicator for plasma sterilization according to claim 1, wherein the azo compound is an azo compound which causes a change in color owing to a reaction at a tertiary nitrogen atom included therein with the mercapto group or the dithiocarbamyl group of the compound.

* * * * *